(12) United States Patent
Kreuter et al.

(10) Patent No.: US 9,248,156 B2
(45) Date of Patent: Feb. 2, 2016

(54) **USE OF EXTRACTS OR MATERIALS EXTRACTED FROM *PIPER CUBEBA* L. AS AN EFFECTIVE COMPONENT IN A DRUG FOR THE TREATMENT OF CANCER DISEASES**

(71) Applicants: Matthias-Heinrich Kreuter, Walenstadt (CH); Jian Ying Yam, Basel (CH); Karin Berger-Buter, Witterswil (CH)

(72) Inventors: Matthias-Heinrich Kreuter, Walenstadt (CH); Jian Ying Yam, Basel (CH); Karin Berger-Buter, Witterswil (CH)

(73) Assignee: Viridis Pharmaceutical Limited, Road Town, Tortola (VG)

( * ) Notice: Subject to any disclaimer, the term of this patent is extended or adjusted under 35 U.S.C. 154(b) by 0 days.

(21) Appl. No.: 13/780,129

(22) Filed: Feb. 28, 2013

(65) Prior Publication Data

US 2013/0251826 A1    Sep. 26, 2013

Related U.S. Application Data

(63) Continuation of application No. 12/673,656, filed as application No. PCT/CH2008/000350 on Aug. 15, 2008, now Pat. No. 8,404,286.

(30) Foreign Application Priority Data

Aug. 16, 2007    (CH) ...................... 1289/07

(51) Int. Cl.
*A61K 36/00* (2006.01)
*A61K 36/67* (2006.01)

(52) U.S. Cl.
CPC ...................... *A61K 36/67* (2013.01)

(58) Field of Classification Search
None
See application file for complete search history.

(56) References Cited

U.S. PATENT DOCUMENTS

| | | |
|---|---|---|
| 2003/0228383 A1 | 12/2003 | Doshi et al. |
| 2004/0126441 A1 | 7/2004 | Pushpangadan et al. |
| 2005/0154215 A1* | 7/2005 | Silva et al. ............ 549/320 |
| 2007/0248693 A1* | 10/2007 | Mazzio et al. ............ 424/725 |

FOREIGN PATENT DOCUMENTS

| | | |
|---|---|---|
| EP | 1 094 813 B1 | 10/2003 |
| JP | 2000-95649 A | 4/2000 |
| WO | WO 03/047551 A1 | 6/2003 |

OTHER PUBLICATIONS

Wahyono et al., "Isolation of Tracheospasmolytic Compounds From *Piper cueba* Fruits", Majalah Farmasi Indonesia, 14(3), pp. 119-123 (2003).
Subramanian et al., "Pharmaco-phytochemical Studies On Fruits Of *Piper cubaba*", Advances in Plant Sciences, vol. 6, No. 2, pp. 329-338 (1993).
Bos et al., "Essential Oil Constituents of *Piper Cubeba* L. fils. from Indonesia", Journal of Essential Oil Research, 19 (1), pp. 14-17 (2007).
Sumathykutty et al., "Essential Oil Constituents of Some *Piper* Species", Flavour and Fragrance Journal, vol. 14, No. 5, pp. 279-282 (1999).
Chatterjee et al., "Spectral Properties of Cubebin Piper-Cubeba-D", Journal of the Indian Chemical Society, 45(8), pp. 723-725 (Jan. 1, 1968).
Dasgupta et al., "Medicinal Species of *Piper*, Pharmacognostic Delimitation", Quarterly Journal of Crude Drug Research, 18(1), pp. 17-25 (Jan. 1, 1980).
Choi et al., "Investigations of Anti-Inflammatory and Antinociceptive Activities of *Piper cubeba*, *Physalis angulata* and *Rosa hybrida*", Journal of Ethnopharmacology, 89(1), pp. 171-175 (Nov. 11, 2003).
Hunnis, Pharmazeuticsches Worterbuch, 8th Edition, pp. 1084-1085 (1998).
Seideman, "World Spice Plants", Springer-Verlag, p. 291 (2005).
Reichert et al., "Stable Expression of the Human 5α-Reductase Isoenzymes Type I and Type II in HEK293 Cells to Identify Dual and Selective Inhibitors", Journal Enzyme Inhibition, 16, pp. 47-53 (2001).
Lindl, "22.4.6 3H-Thymidline Incorporation as Proliferation Control", Zell- and Gewebekultur, 4th Revised Edition, Specktrum Akademisher Verlag., Heidelberg, pp. 252-253 (2000).

* cited by examiner

*Primary Examiner* — Qiuwen Mi
(74) *Attorney, Agent, or Firm* — McDonnell Boehnen Hulbert & Berghoff LLP

(57) ABSTRACT

The present invention is directed to the use of extracts or of extract compounds from *Piper cubeba* L. as active components in a medicament for the treatment of cancer. The invention also relates to a method for the preparation of a dry extract from the fruit of *Piper cubeba* L.

13 Claims, 6 Drawing Sheets

USE OF EXTRACTS OR MATERIALS EXTRACTED FROM *PIPER CUBEBA* L. AS AN EFFECTIVE COMPONENT IN A DRUG FOR THE TREATMENT OF CANCER DISEASES

The present invention is directed to the use of extracts or of extract compounds from *Piper cubeba* L. as active components in a medicament for the treatment of cancer.

Uses of *Piper cubeba* L. compositions are described for example in Hunnius, Pharmazeutisches Wörterbuch, 8$^{th}$ edition, 1998, pages 1084 to 1085.

Herein are described popular applications, such as the treatment of headache as well as the use as diuretic, urine disinfectant and stomachic.

As drug is used the immature fruit, from which also the cubeben-oil, the essential oil of the cubeben, is obtained by steam distillation.

Oleum Cubebae is applied in the same indications as the fruits.

According to J. Seidemann in "World Spice Plants", Springer-Verlag, 2005, page 291 *Piper cubeba* L. is used for the aromatization of liqueur, ginger bread, and honey bread. As product is used the essential oil that is obtainable from the immature fruit.

In JP 2000-095649 A are described extracts, among others also from the cubeben fruit that are obtained by means of a hydrophilic solvent, for example acetone, methanol and ethanol, or their mixtures with water. Thus, such extracts contain both the essential oil and hydrophilic substances.

These extracts shall act as testosteron-5α-reeducate inhibitors. Thereby these extracts shall influence positively the growth of hair.

These extracts shall also serve for the treatment of benign prostate hyperplasia.

In this document are given in table 1 $IC_{50}$-values that are referred to the inhibition of the testosteron-5α-reductase.

The extract of cubeben inhibits according to this table the enzyme for 50% at a concentration of 0.79 mg/ml.

A. Chatterjee et. al., Jour. Indian Chem. Soc., Vol. 45, No. 8, 1968, pages 723 to 725 describes the spectral characteristics of the pure substance Cubebin. This chemical compound was isolated from an alcoholic extract of the defatted fruits of *Piper cubeba* L.

A. Dasgupta et. al., Quart. J. Crude Drug Ret., 18, (1980), No. 1, pages 17 to 25 describes the use of the essential oil of *Piper cubeba* L. for the treatment of for example cystitis, and gonorrhoea.

Eun-Mi Choi et. al., Journal of Ethnopharmacology, Elsevier Scientific Publishers Ltd., 89, 2003, pages 171 to 175 describes anti-inflammatory characteristics of an extract prepared with 80% methanol from dried fruits of *Piper cubeba* L.

During a screening-process were tested several tropical medicinal plants upon their activity against tumor cells in vitro.

It was found quite surprisingly that an ethanolic extract from immature fruits of cubeben kills all tested tumor cells.

As predominantly the essential oil of the cubeben fruits is used in medicine it was obvious to extract the fruits with a suitable extracting agent in order to obtain the essential oil.

This was realized by an exhausting extraction with hexane.

The fruits, exempted in this way from the essential oil, were for the sake of completeness extracted additionally with 90% aqueous ethanol in order to obtain medium polar extract compounds.

Both the obtained essential oil and the ethanolic secondary extract were then tested upon their activity against tumor cells.

As expected it was found that the obtained essential oil killed all tested tumor cells. This points to the fact that the observed cytotoxic effect is of unspecific nature and thus demonstrates no antitumor effect.

But quite surprisingly it was found that the ethanolic secondary extract indeed did not kill directly any of the tested tumor cells but changed in some tumor cells their proliferation behaviour.

Such tumor cells proved to be as especially sensitive against the ethanolic secondary extract that need for their growth sex hormones as growth factors. As examples are mentioned the breast cancer cell line MCF 7 and the prostate cancer cell line LnCAP. This observation allows the conclusion that the proliferation inhibiting activity may not rely primary on an inhibition of the testosteron-5α-reductase as this is irrelevant for the growth of the breast cancer cell line MCF 7.

It is an object of the present, invention to provide a process for the preparation of an extract from fruits of *Piper cubeba* L.

This extract shall be free or nearly free from cytotoxic essential oils.

This extract shall inhibit the growth especially of such tumor cells that need for their growth sex hormones as growth factors.

This extract shall show anti-androgenic and/or anti-estrogenic activities.

This extract shall antagonize the activities of the sex hormone dihydrotestosterone, abbreviated with DHT, especially its proliferation enhancing and anti-apoptotic effect on prostate cancer cells.

These objects are attained with the present invention.

The invention is characterized by the characteristics as defined in the independent claims.

Preferred embodiments are defined in the dependent claims.

In the following part are described possible embodiments of the present invention.

Thereby is made also reference to the figures.

Figure 1A:
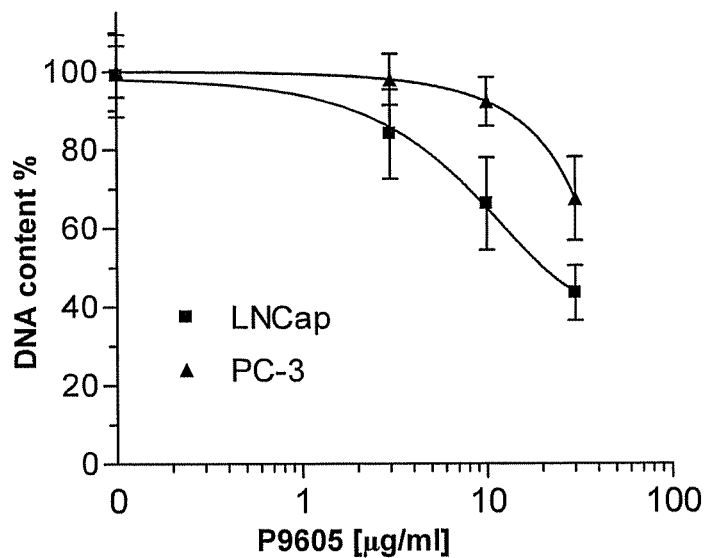
FIG. 1a shows the anti-proliferate effect of the extract prepared according to example 1 on LNCap and PC-3 cells.

The following examples illustrate the present invention.

EXAMPLE 1

Preparation of a Liquid Extract 110 g of immature, dried fruits of *Piper cubeba L.* having a grinding fineness from 0.1 mm to 0.9 mm were extracted under stirring at a temperature between 10° C. and 20° C. during 8 hours with 0.5 liters of hexane. The hexane layer charged with the essential oils and highly lipophilic components was they separated. This procedure was carried out once more whereby the extraction time was limited to 2 hours.

The so defatted fruits were then dried in a vacuum cabinet at a temperature of 40° C. until constancy of the weight. There were obtained 92 g of defatted drug material.

Then the so treated fruits were extracted under stirring at a temperature between 20° C. and 30° C. during 2 hours with a mixture of 90 parts by weight of ethanol and 10 parts by weight of water.

The weight ratio between the drug and the extraction mixture was 1:5.

The so extracted drug was separated by means of layer filtration. There were obtained 380 g of a dark brown liquid extract having a dry substance content of 1.92 m/m %, corresponding to a yield of extract compounds of 7.3 g absolute from 92 g defatted fruits.

This extract is denoted in the following part as P9605.

This extract contains 20 m/m % of Cubebin, referred to the dry substance content.

EXAMPLE 2

Preparation of a Dry Extract

A liquid extract obtained according to example 1 was added dose by dose into an evaporator at a temperature of 40° C. and the evaporation was started under vacuum (300 mbar to 20 mbar) and elevated temperature (40° C. to 55° C.)

During the distillation the remaining part of the fluid extract was added continuously dose by dose into the evaporator until the total amount of the fluid extract has been added and until in the obtained spissum extract a dry substance content from 30 to 40 m/m % was reached.

There were obtained 20.0 g of spissum extract with a dark brown colour, free flowing and of homogenous consistency. The spissum extract showed a dry substance content of 36.5 m/m %, what corresponds to a content of extract compounds of 7.3 g.

This concentrated spissum extract was mixed homogenously with 7.8 g of an aqueous 40 m/m % a gum arabic solution and then dried in a dryer under vacuum, at a pressure from 150 mbar to 10 mbar and a temperature from 40° C. to 55° C.

There were obtained 10.4 g of an ochre brown dry extract having a content of 30 m/m % of gum arabic as auxiliary agent.

EXAMPLE 3

Preparation of a Dry Extract-Oil Suspension

A liquid extract obtained according to example 1 was added dose by dose into an evaporator at a temperature of 40° C., and the evaporation was started under vacuum (300 mbar to 20 mbar) and elevated temperature (40° C. to 55° C.)

During the distillation the remaining part of the fluid extract was added continuously dose by dose into the evaporator until the total amount of the fluid extract has been added and until in the obtained spissum extract a dry substance content from 10 to 20 m/m % was reached.

There were obtained 54.0 g of spissum extract with a dark brown colour, free flowing and of homogenous consistency. The spissum extract showed a dry substance content of 15.7 m/m %, what corresponds to a content of extract compounds of 7.3 g.

This spissum extract of low viscosity was mixed with 6.8 g of middle chain triglycerides (Ph. Eur.) and 0.5 g of soya-lecithin (ÖAB 90) and added dose by dose into an evaporator at a temperature of 40° C. The evaporation of this mixture was carried out during such a long time under vacuum (300 mbar to 40 mbar) and at elevated temperature (40° C. to 50° C.) until in the obtained spissum extract a dry substance content from 70 to 80 m/m % was reached.

There was obtained a viscous spissum extract that was then dried in a dryer under vacuum at a pressure from 150 mbar to 10 mbar and a temperature from 40° C. to 55° C. until a dry substance content of 99.5 m/m % was reached.

There were obtained 14.9 g of a dark brown dry extract-oil suspension having a content of 49 m/m % of middle chain triglycerides and 3.36 m/m % soya-lecithin as auxiliary agents.

EXAMPLE 4

Inhibition of the Cell Proliferation

With the liquid extract P9605 prepared according to example 1 were carried out cell proliferation tests. As control was carried along a typical substance of content of the cubeben fruits, the lignan Cubebin.

For the measurement of the inhibition of the cell proliferation this extract was added to LNCap and to PC-3 cells. The so treated cells were cultivated during 4 days in 10 FBS culture medium.

For comparison the pure lignan Cubebin, that is contained in the extract prepared according to the invention and according to example 1 in an amount up to 20 m/m % of the dry substance, was added also to LNCap and to PC-3 cells. The so treated cells were cultivated during 4 days in 10% PBS culture medium.

Thereby it was proceeded according to T. Lindl, Zell-und Gewebekultur, 4$^{th}$ revised edition, 2000, Spektrum Akademischer Verlag, Heidelberg.

All obtained dates are given in percents with regard to the solvent control (test without extract and without Cubebin); there are given the average values with Standard deviation from 4 experiments with 3-fold repetition.

Figure 1B:
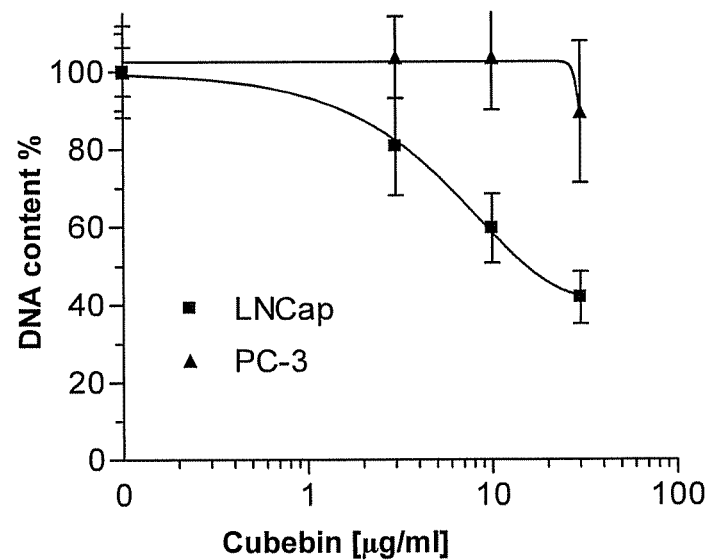
FIG. 1b shows the anti-proliferate effect of the pure substance Cubebin on LNCap and PC-3 cells.

From the datas as shown in FIGS. 1*a* and 1*b* it is obvious that both the extract prepared according to the invention and the pure substance Cubebin show an anti-proliferate effect on LNCap and PC-3 cells in dependency of the respective dose.

The inhibition was more pronounced on LNCap cells than on PC-3 cells.

It is obvious from FIGS. 1a and 1b that the inhibitive activity of the extract P9605 prepared according to example 1 is much stronger than this would be explainable by its content of Cubebin. The extract contains only 20 m/m % of Cubebin, but shows the same (LNCap) or a stronger (PC-3) inhibitive activity.

EXAMPLE 5

Inhibition of the DNA Synthesis

With the liquid extract P9605 prepared according to example 1 were carried out DNA synthesis tests.

For the measurement of the inhibition of the DNA synthesis the extract prepared according to the present invention was added to LNCap cells. The so treated cells were cultivated during 4 days in 10% FBS culture medium.

Then was measured the amount of incorporated $^3$H-thymidin.

Thereby it was proceeded according to T. Lindl, Zell-und Gewebekultur, $4^{th}$ revised edition, 2000, Spektrum Akademischer Verlag, Heidelberg.

All obtained datas are given in percents with regard to the solvent control (test without extract); there are given the average values with Standard deviation from 4 experiments with 3-fold repetition.

Figure 2:
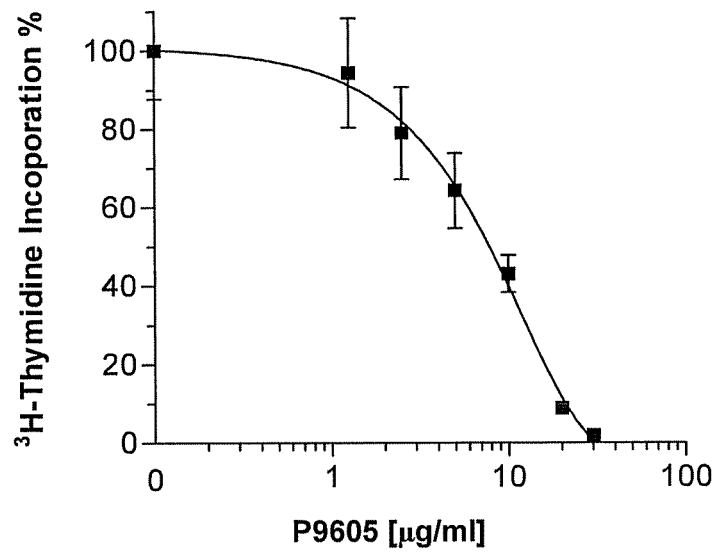
FIG. 2 shows the inhibition of the DNA-synthesis of LNCap cells with the extract prepared according to example 1.

It is obvious from the datas shown in FIG. 2 that the extract prepared according to the present invention inhibits the DNA synthesis in dependency of the respective dose.

EXAMPLE 6

Anti-Androgenic Effect on the Cell Proliferation

The anti-androgenic effect on the androgen dependent cell proliferation of the liquid extract P9605 prepared according to example 1 was determined.

Thereby the extract prepared according to the present invention was added to LNCap cells. The so treated cells were cultivated during 6 days in 10% CSS culture medium.

This cultivation was realized once without the addition of dihydrotestosterone, abbreviated with DHT, and once with the addition of 1 nM DHT.

Then was determined the influence of the extract prepared according to the present invention on the cell proliferation of the tumor cells on the basis of the DNA content.

All obtained datas are given in percents with regard to the solvent control (test without extract); there are given the average values with Standard deviation from 4 experiments with 3-fold repetition.

Figure 3:
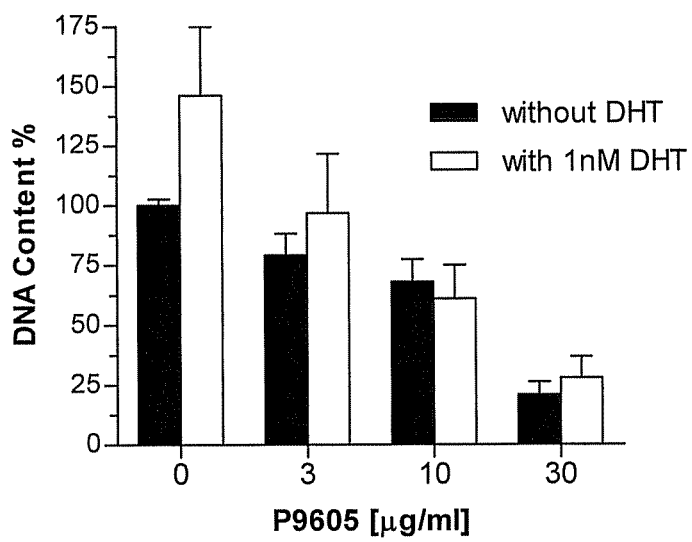
FIG. 3 shows the anti-androgenic effect of the extract prepared according to example 1 on the androgen-dependent cell proliferation on LNCap cells.

It is obvious from the dates shown in FIG. 3 that the extract prepared according to the present invention overexcites in dependency of the dose the stimulating effect of DHT on the cell proliferation of the tumor cells and in addition lowers the basal proliferation of the cells.

It is known that DHT enhances the cell proliferation; see the control value at zero.

EXAMPLE 7

Anti-Androgenic Effect on the DNA Synthesis

The anti-androgenic effect on the DNA synthesis of the liquid extract P9605 prepared according to example 1 was determined.

Thereby the extract prepared according to the present invention was added to LNCap cells. The so treated cells were cultivated during 6 days in 10% CSS culture medium.

This cultivation was realized once without the addition of dihydrotestosterone, abbreviated with DHT, and once with the addition of 1 nM DHT.

Then was measured the amount of incorporated $^3$H-thymidin.

Thereby it was proceeded according to T. Lindl, Zell-und Gewebekultur, $4^{th}$ revised edition, 2000, Spektrum Akademischer Verlag, Heidelberg.

All obtained datas are given in percents with regard to the solvent control (test without extract); there are given the average values with Standard deviation from 4 experiments with 3-fold repetition.

Figure 4:
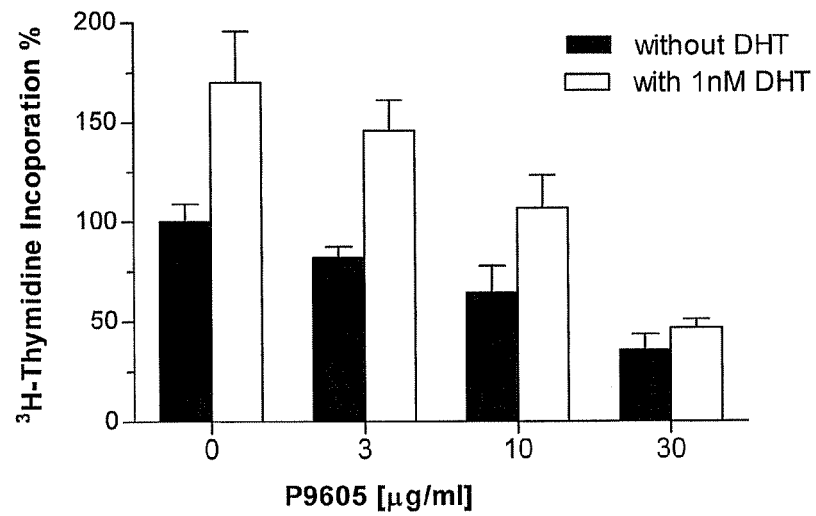
FIG. 4 shows the anti-androgenic effect of the extract prepared according to example 1 on the DNA-synthesis of LNCap cells.

It is obvious from the datas shown in FIG. 4 that the extract prepared according to the present invention overexcites in dependency of the dose the stimulating effect of DHT on the DNA synthesis of the tumor cells and in addition lowers the basal DNA synthesis of the cells.

It is known that DHT enhances the DNA synthesis; see the control value at zero.

EXAMPLE 8

Anti-Estrogenic Effect on the DNA Synthesis of Breast Tumor Cells

The anti-estrogenic effect on the DNA synthesis of breast tumor cells of the liquid extract P9605 prepared according to example 1 was determined.

Thereby MCF-7 cells were cultivated during 3 days in 10% CSS culture medium to which were added different concentrations of estradiol.

This cultivation was realized once without the addition of the extract prepared according to the present invention and once with the addition of 10 μg/ml of the extract.

Then was measured the amount of incorporated $^3$H-thymidin.

Thereby it was proceeded according to T. Lindl, Zell-und Gewebekultur, $4^{th}$ revised edition, 2000, Spektrum Akademischer Verlag, Heidelberg.

All obtained results are given in DPM (radioactive degradation per minute); there are given the average values with Standard deviation from 4 experiments with 3-fold repetition.

Figure 5:
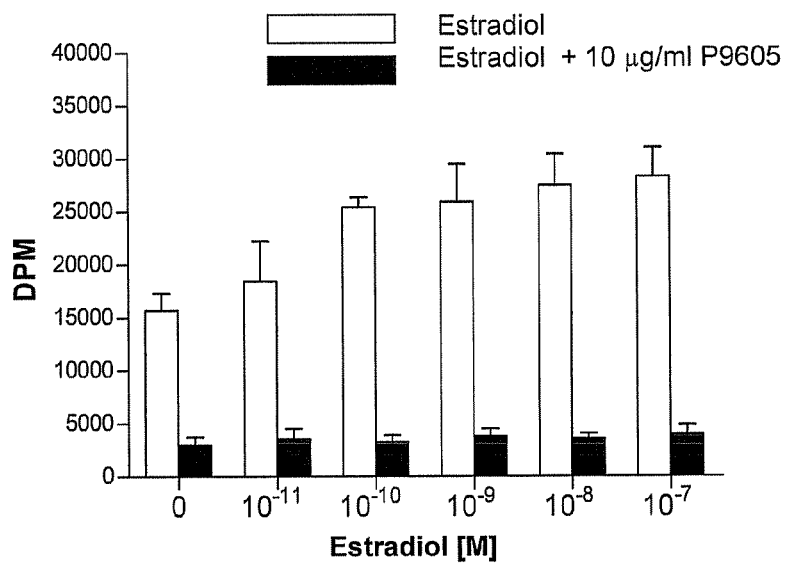
FIG. 5 shows the anti-estrogenic effect of the extract prepared according to example 1 on the DNA-synthesis of MCF-7 cells.

It is obvious from the datas shown in FIG. 5 that the extract prepared according to the present invention stops completely or nearly completely the stimulation of the DNA synthesis of breast cancer cells by estradiol.

It is known that estradiol enhances the DNA synthesis of breast cancer cells; see the control value at zero.

EXAMPLE 9

Inhibition of the 5α-Reductase Type II Activity

The inhibition of the 5α-reductase type II activity by means of the liquid extract P9605 prepared according to example 1 was determined.

The assay was realized with a homogenate of HEK293 cells that over express the 5α-reductase type II (Reichert W., Hartmann R. N. and Jose J. 2001, Journal Enzyme Inhibition, Vol. 16, 47-53).

The influence of the extract prepared according to the present invention and of the pure substance Cubebin on the activity of the 5α-reductase type II was determined by means of the measurement of the conversion of $^3$H-testosterone in $^3$H-DHT.

As control substance was used the known 5α-reductase inhibitor "Finasterid".

All obtained datas are given in percents with regard to the solvent control (test without extract); there are given the average values with Standard deviation from 4 experiments with 3-fold repetition.

Figure 6A:
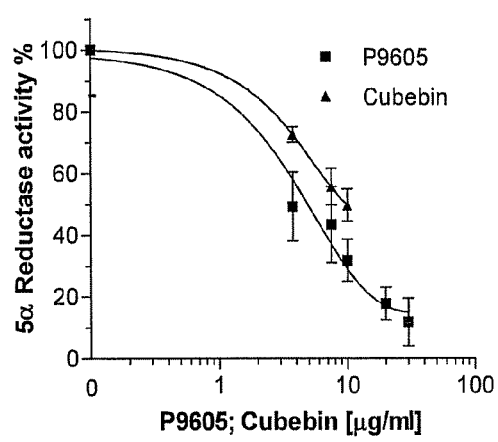
FIG. 6a shows the inhibiting effect of the extract prepared according to example 1 and of the pure substance Cubebin on the activity of 5α-reductase type II.

It is obvious from the datas shown in FIG. 6a that both the extract prepared according to the present invention and the pure substance Cubebin show an inhibitive effect on the activity of the 5α-reductase type II.

The inhibition is stronger with the extract than with the pure substance Cubebin.

The extract inhibits with an $IC_{50}$-value of 3.6 μg/ml, whereas the pure Substance Cubebin inhibits with an $IC_{50}$-value of 9.9 μg/ml.

Figure 6B:
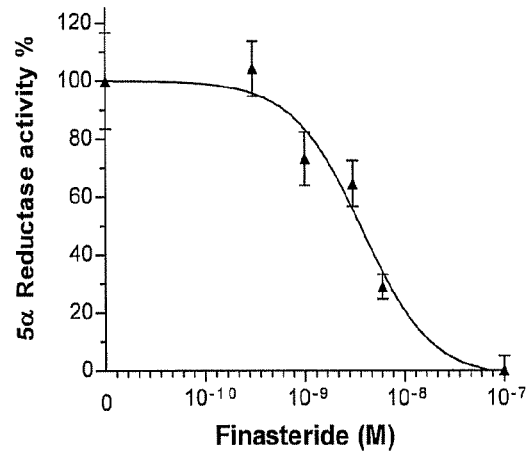
FIG. 6b shows the inhibiting effect of the known 5α-reductase inhibitor "Finasterid" on the activity of 5α-reductase type II.

The course of the dose activity graph of the extract and of the pure substance Cubebin are analogous to the course of the dose activity graph of the known 5α-reductase inhibitor "Finasterid" (FIG. 6b).

EXAMPLE 10

Increase of Apoptosis

The induction of apoptosis by means of the liquid extract P9605 prepared according to example 1 was determined.

As preliminary test was added for the measurement of the induction of apoptosis the tumor necrosis factor TNF-α alone as well as in combination with 100 nM dihydrotestosterone, abbreviated with DHT, to LNCap cells. The so treated Cent were cultivated during 2 days in 10% FBS culture medium.

The apoptosis of the cells was measured by applying a commercial apoptosis-immuno-assay-kit in which are detected specifically the DNA and histon fragments that are present as mono and oligonucleosomes.

Figure 7A:
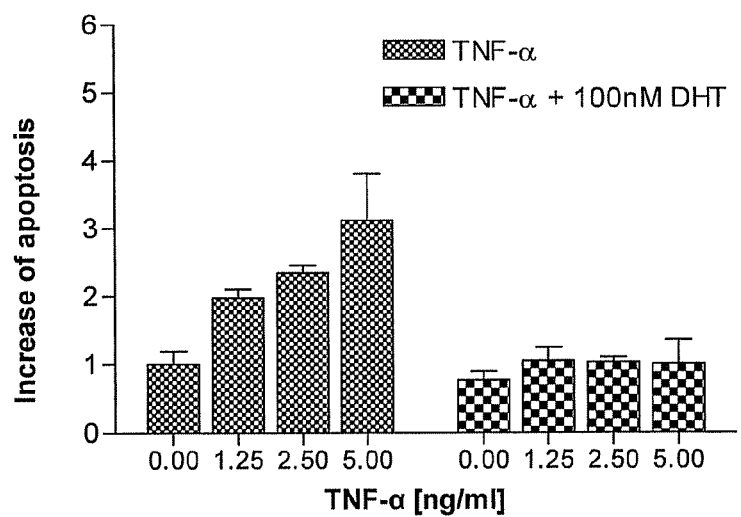
FIG. 7a shows that TNF-α induces the apoptosis of the tumor cells in dependency of the dose, and that this effect is abolished completely with DHT in the tumor cells.

It is obvious from the datas shown in FIG. 7a that TNF-α induces the apoptosis of the tumor cells in dependency of the dose.

This effect is revoked completely or nearly completely with DHT in the tumor cells.

Analogous experiments were carried out with DHT alone as well as in combination with 10 μg/ml of the extract prepared according to the present invention.

Figure 7B:
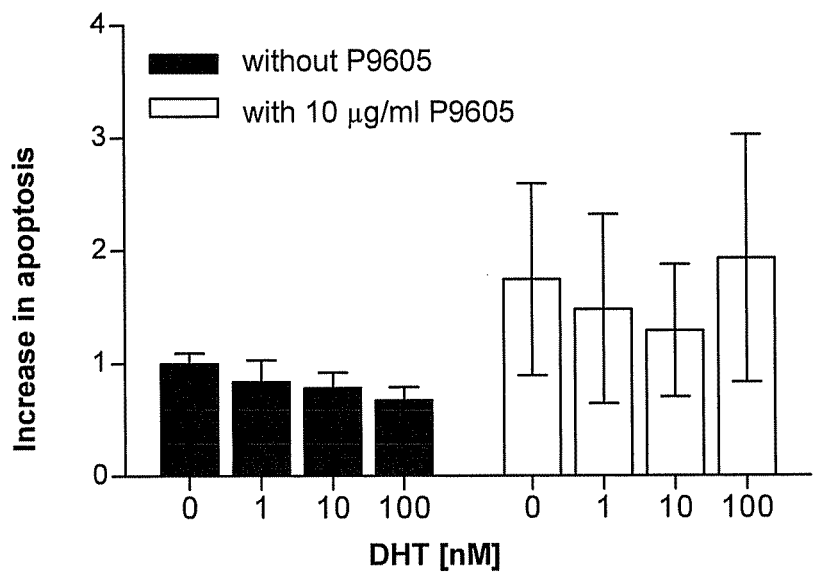
FIG. 7b shows that the anti-apoptotic effect of DHT is abolished by the extract prepared according to example 1.

It is obvious from the datas shown in FIG. 7b that the anti-apoptotic activity of DHT is revoked by the extract prepared according to the present invention.

EXAMPLE 11

Inhibition of the Secretion of the Prostate Specific Antigen

The inhibition of the prostate specific antigen (PSA) by means of the liquid extract P9605 prepared according to example 1 was determined.

Thereby in one experiment LNCap cells were cultivated during 2 days in 10% CSS culture medium to which were added different concentrations either of the extract prepared according to the present invention or of the pure substance Cubebin.

Then was measured the secreted PSA amount in the cell supernatant by means of an immuno-Assay. Additionally the amount of DNA was determined.

Figure 8:
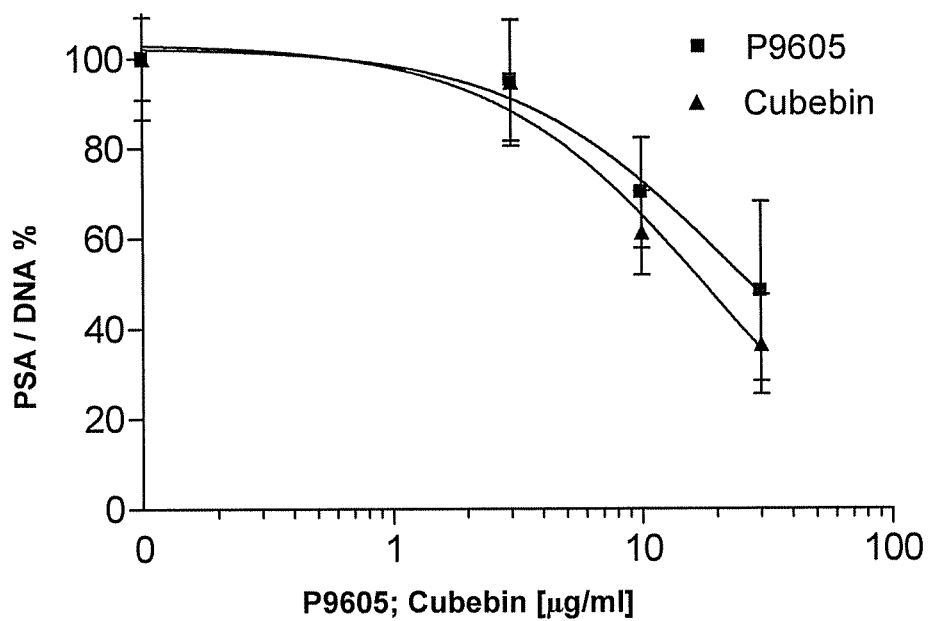
FIG. 8 shows that both the extract prepared according to example 1 and the pure substance Cubebin inhibit the secretion of the prostate specific antigen (PSA) in dependency of the respective dose.

In FIG. 8 is shown the proportion in percents of the amount of PSA to the amount of DNA.

There are given the average values with Standard deviation from 4 experiments with 3-fold repetition.

It is obvious from the dates shown in FIG. 8 that both the extract and the pure substance Cubebin inhibit the secretion of the prostate specific antigen (PSA) in dependency of the respective dose.

In a second experiment LNCap cells were cultivated during 2 days in 10% CSS culture medium to which were added different concentrations of dihydrotestosterone, abbreviated with DHT.

This cultivation was realized once without the addition of the extract prepared according to the present invention and once with the addition of 10 μg/ml of extract.

Then was measured the secreted PSA amount in the cell supernatant by means of an immuno-Assay. Additionally the amount of DNA was determined.

Figure 9:
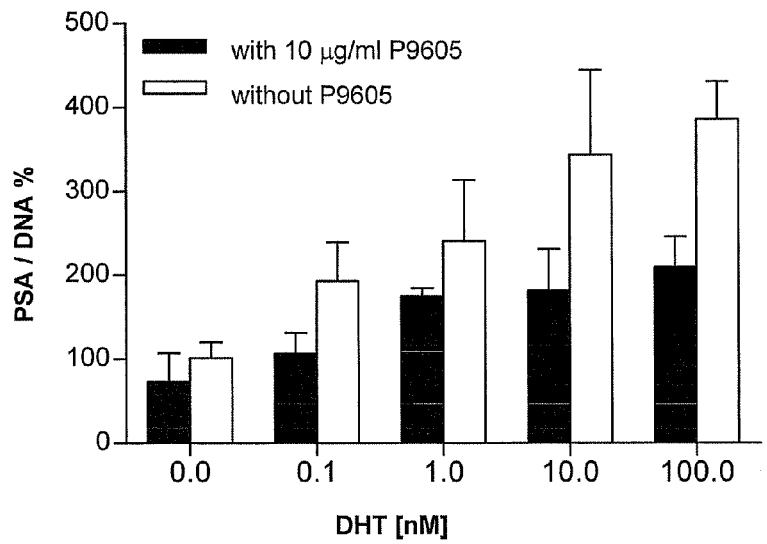
FIG. 9 shows that the extract prepared according to example 1 inhibits strongly the with DHT induced secretion of the prostate specific antigen (PSA).

In FIG. 9 is shown the proportion in percents of the amount of PSA to the amount of DNA.

There are given the average values with Standard deviation from 4 experiments with 3-fold repetition.

It is obvious from the dates shown in FIG. 9 that the secretion of the prostate specific antigen (PSA) induced by DHT is strongly inhibited by the extract prepared according to the present invention.

EXAMPLE 12

Generation of Androgen Receptors

The influence of the generation of androgen receptors by means of the liquid extract P9605 prepared according to example 1 was determined.

Thereby in one experiment LNCap cells were cultivated during 2 days in 10% FBS culture medium to which were added different concentrations either of the extract prepared according to the present invention or of the pure substance Cubebin.

Then was determined the change of the amount of the androgen receptor by means of the Westernblot analysis.

Figure 10:
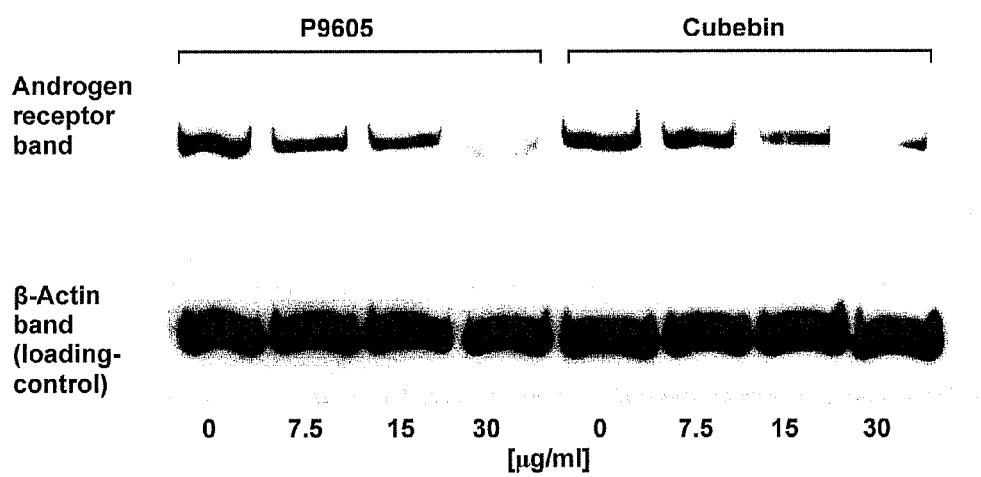
FIG. 10 shows that the androgen receptor concentration in LNCap cells is reduced increasingly in dependency of the dose both by the treatment with the extract prepared according to example 1 and by the treatment with the pure substance Cubebin.

In FIG. 10 are shown the bands of the androgen receptor.

The androgen receptor denseness in LNCap cells is reduced increasingly in dependency of the dose both by the treatment with the extract prepared according to the present invention and by the treatment with the pure substance Cubebin.

CONCLUSIONS

In the examples 1 to 3 is shown by which combinations of process steps extracts of cubeben fruits may be prepared that are free or nearly free of essential oil, show new characteristics and met the objects of the present invention.

Examples 4 to 12 demonstrate the antitumor activity of the extracts prepared according to the present invention and illustrate the activity mechanisms that form the basis of the activity against hormone dependent tumor cells. These examples show the high therapeutical potential of the extracts prepared according to the present invention, especially for the therapy of malign diseases which progression is influenced by female or male sex hormones When considering the efficacy ($IC_{50}$:3.6 μg/ml) of the extracts prepared according to the present invention against the human 5α-reductase in comparison to the activity mentioned in JP 2000-095649 A ($IC_{50}$: 790 μg/ml) then it becomes obvious that the extracts prepared according to the present invention have an about 200-fold higher activity and thus open also for the treatment of the prostate hyperplasia quite new possibilities.

The invention claimed is:

1. A method of treating cancer, comprising the administration of an extract of fruit of *Piper cubeba* L. to a person in need of such treatment, wherein the extract is prepared by a process comprising defatting ground immature *Piper cubeba* L. fruit having a particle size of 0.1 mm to 0.9 mm with a solvent selected from hexane and isopentane to produce defatted fruit; and extracting the defatted fruit with at least one alcohol or with a mixture of at least one alcohol and water.

2. A method according to claim 1 wherein the cancer is selected from the group consisting of prostate cancer, testicular cancer, breast cancer, uterine cancer, including their metastases, and benign prostate hyperplasia.

3. A method of treating cancer according to claim 1, wherein the defatting is conducted at a weight ratio of fruit to solvent of 1:6 to 1:12 at a temperature of from 5° C. to 15° C. for 2 to 4 hours.

4. A method of treating cancer according to claim 1, wherein the process further comprises, subsequent to extracting the defatted fruit with at least one alcohol and water, removing the extracted fruit parts to produce a liquid extract;

adding to the liquid extract an auxiliary agent;

concentrating the liquid extract to a concentration of alcohol between 0.1 and 10 m/m %; and drying the liquid extract to produce a dry extract.

5. A method of treating cancer according to claim 4, wherein the auxiliary agent is mannitol; the liquid extract is concentrated to an alcohol concentration of 5 m/m %; the drying is spray drying, belt drying or blade drying; and the dry extract is free or nearly free of α-cubebene and β-cubebene.

6. A method of treating cancer according to claim 1, wherein the extracting the defatted fruit is carried out with a mixture of ethanol and water having a mass ratio of ethanol to water of about 1:1 to about 9:1.

7. The method of treating cancer according to claim 1, wherein the extracting defatted fruit is conducted with an ethanol/water mixture having a mass ratio of ethanol to water of 4:1 to 9:1 at a temperature from 20° C. to 60° C. and for 2 to 4 hours.

8. A methods of antagonizing the activities of the sex hormone dihydrotestosterone comprising the administration of an extract of fruit of *Piper cubeba* L. to a patient in need of such treatment, wherein the extract is prepared by a process comprising defatting ground immature *Piper cubeba* L. fruit having a particle size of 0.1 mm to 0.9 mm with a solvent selected from hexane and isopentane to produce defatted fruit; and extracting the defatted fruit with at least one alcohol or with a mixture of at least one alcohol and water.

9. A method of treating cancer according to claim 8, wherein the defatting is conducted at a weight ratio of fruit to solvent of 1:6 to 1:12 at a temperature of from 5° C. to 15° C. for 2 to 4 hours.

10. A method of treating cancer according to claim 8, wherein the process further comprises, subsequent to extracting the defatted fruit with at least one alcohol and water, removing the extracted fruit parts to produce a liquid extract;

adding to the liquid extract an auxiliary agent;

concentrating the liquid extract to a concentration of alcohol between 0.1 and 10 m/m %; and drying the liquid extract to produce a dry extract.

11. A method of treating cancer according to claim 10, wherein the auxiliary agent is mannitol; the liquid extract is concentrated to an alcohol concentration of 5 m/m %; the drying is spray drying, belt drying or blade drying; and the dry extract is free or nearly free of α-cubebene and β-cubebene.

12. A method pace that according to claim 8, wherein the extracting the defatted fruit is carried out with a mixture of ethanol and water having a mass ratio of ethanol to water of about 1:1 to about 9:1.

13. The method of treating cancer according to claim 8, wherein the extracting defatted fruit is conducted with an ethanol/water mixture having a mass ratio of ethanol to water of 4:1 to 9:1 at a temperature from 20° C. to 60° C. and for 2 to 4 hours.

* * * * *